United States Patent [19]

Vinegar et al.

[11] Patent Number: 4,571,491
[45] Date of Patent: Feb. 18, 1986

[54] METHOD OF IMAGING THE ATOMIC NUMBER OF A SAMPLE

[75] Inventors: Harold J. Vinegar; Scott L. Wellington, both of Houston, Tex.

[73] Assignee: Shell Oil Company, Houston, Tex.

[21] Appl. No.: 566,618

[22] Filed: Dec. 29, 1983

[51] Int. Cl.[4] ............................................. G01D 18/00
[52] U.S. Cl. .................................. 250/252.1; 378/207
[58] Field of Search ..................... 378/5, 99, 100, 207; 250/255, 252.1

[56] References Cited

U.S. PATENT DOCUMENTS 4,029,963  6/1977  Alvarez et al. ..................... 250/360
4,283,629  8/1981  Habermehl et al. ................ 378/197

OTHER PUBLICATIONS

"Estimation of Chemical Composition and Density from Computed Tomography Carried Out at a Number of Energies", W. D. McDavid et al., *Investigative Radiology*, vol. 12, No. 2, Mar. 1977, pp. 189–194.
"Initial Results With Preconstruction Dual-Energy Computed Tomography (PREDECT)", W. H. Marshall, Jr. et al., *Radiology* 140, pp. 421–430, Aug. 1981.
"Energy-Selective Reconstructions in X-Ray Computerized Tomography", R. E. Alvarez et al., *Phys. Med. Biol.*, 1976, vol. 21, No. 5, pp. 733–744.
"Generalized Image Combinations in Dual KVP Digital Radiography", L. A. Lehmann et al., *Medical Physics*, vol. 8, No. 5, Sep./Oct. 1981, pp. 659–667.
"Split Xenon Detector for Tomochemistry in Computed Tomography", A. Fenster, *Journal of Computer Assisted Tomography*, vol. 2, No. 3, Jul. 1978, pp. 243–252.
"Split-Filter Computed Tomography: A Simple Technique for Dual Energy Scanning", B. Rutt et al., *Journal of Computer Assisted Tomography*, vol. 4, No. 4, Aug. 1980, pp. 501–509.
"Soil Bulk Density Analysis in Three Dimensions by Computed Tomographic Scanning", A. M. Petrovic et al., *Soil Science Society of America Journal*, vol. 46, No. 3, May–Jun. 1982, pp. 445–450.
"Clinical Application of Compton and Photo-Electric Reconstruction in Computed Tomography: Preliminary Results", D. E. Arvin et al., *Investigative Radiology*, Assn of Univ. Radiologists, 27th Ann. Meeting, N.Y., May 1979, pp. 217–221.
"A Method for Selective Tissue and Bone Visualization Using Dual Energy Scanned Projection Radiography", W. R. Brody et al., *Medical Physics*, vol. 8, No. 3, May/Jun. 1981, pp. 353–357.

*Primary Examiner*—Janice A. Howell

[57] ABSTRACT

A method of obtaining an atomic number image of an unknown material. A plurality of calibration materials which have a plurality of different known atomic numbers and densities are scanned with a CAT at first and second energies to determine the attenuation coefficients for the plurality of calibration materials at these energies. The energy-dependent coefficients at the first and second energies are determined from the attenuation coefficients for the plurality of calibration materials at the first and second energies according to a predetermined relation. The unknown material is scanned with a CAT at the first and second energies to determine the attenuation coefficients at a plurality of points in a cross section of the unknown material at these energies. The determined energy-dependent coefficients and the determined attenuation coefficients for the unknown material at the first and second energies are used to determine an atomic number image for the unknown material.

24 Claims, 9 Drawing Figures

METHOD OF IMAGING THE ATOMIC NUMBER OF A SAMPLE

BACKGROUND OF THE INVENTION

This invention relates to computerized axial tomographic analysis and, more particularly, to the determination of an atomic number image for a sample, such as a core sample from a borehole, and to the determination of a density image for the sample that is corrected for the effects of atomic composition of the sample by such analysis.

Atomic number imaging by a computerized axial tomographic scanner (hereinafter referred to as "CAT") is based on the fact that X-ray attenuation depends both on the density and the chemical composition of a material. Between mean energies of 80 keV and 1 MeV X-rays interact with matter predominantly by Compton scattering which is dependent on electron density. For X-ray energies below a mean energy of 80 keV, photoelectric absorption becomes important; this type of interaction is strongly dependent on atomic number. If the attenuation coefficients are measured at two X-ray energies, one in the Compton region and one in the photoelectric region, separate images of density and effective atomic number can be obtained. The prior art has employed preimaging methods involving hardware modifications, such as split-energy detectors or pulse-height counting, and extensive numerical calculation from the raw data. These hardware modifications are expensive to implement and maintain and require software modifications that are system dependent. A typical CAT has 720 detectors, but it may have as many as 1440 detectors. If split-energy detectors are used, 1440 electronic preamplifiers would be required to gather the data collected by the 720 split-energy detectors. If pulse-height counting is employed, a single channel analyzer would be required for each of the 720 channels. In either case the initial cost is high and the maintenance required is extensive. The numerical calculations required with the prior art techniques, such as that disclosed in Alvarez et al., U.S. Pat. No. 4,029,963, generally require solving nonlinear integral equations; these solutions are complex, time consuming and cannot be accomplished in real time.

In addition, prior art CAT systems have not corrected the density image of unknown materials for the effects of atomic composition, because of the complexity and expenses associated with split-energy detectors and pulse-height counting as discussed hereinabove.

Therefore, it is an object of the present invention to provide an atomic number imaging technique that simplifies the calculations required and eliminates the need for specialized hardware and software.

It is a further object of the present invention to provide a method of obtaining a density image of an unknown material that is corrected for the effects of atomic composition of the unknown material.

SUMMARY OF THE INVENTION

In accordance with the present invention there is provided a method of obtaining an atomic number image of an unknown material. A plurality of calibration materials which have a plurality of different known atomic numbers and densities are scanned with a CAT at a first energy to determine the attenuation coefficients for the plurality of calibration materials at the first energy. The plurality of calibration materials are also scanned with a CAT at a second energy to determine the attenuation coefficients for the plurality of calibration materials at the second energy. The energy-dependent coefficients, a and b, at the first and second energies are determined from the attenuation coefficients for the plurality of calibration materials at the first and second energies according to the following equation $$\mu_i = a Z_i^m \rho_i + b \rho_i$$

where $\mu_i$, $Z_i$ and $\rho_i$ are respectively the attenuation coefficient, atomic number and electron density for the $i^{th}$ calibration material, a and b are energy-dependent coefficients and m is a constant between 3.0 and 4.0. The unknown material is scanned with a CAT at said first and second energies to determine the attenuation coefficients at a plurality of points in a cross section of said unknown material at said first and second energies. The determined energy-dependent coefficients and the determined attenuation coefficients for the unknown material at the first and second energies are used to determine an atomic number image for the unknown material.

In addition, the present invention provides a method of obtaining a density image of an unknown material that is corrected for the effects of atomic composition of the unknown material. This method employs the aforesaid steps of dual energy scanning of calibration materials with a CAT, determining the energy-dependent coefficients and dual energy scanning of the unknown material. The determined energy-dependent coefficients and the determined attenuation coefficients for the unknown material at the two energies are used to determine a density image of the unknown material that is corrected for the effects of its atomic composition.

The method of the present invention provides a postimaging technique which is applied to the final image rather than the raw data as is done in the prior art, thereby simplifying the calculations required and also eliminating the need for specialized hardware modifications for each CAT scanner. The subject technique is analytically simple when compared with the complex methods of the prior art, since it is directly calibrated on known materials. Moreover, the method of the present invention is applicable to any CAT without hardware modifications.

Other objectives, advantages and applications of the present invention will be made apparent by the following detailed description of the preferred embodiments of the present invention.

DETAILED DESCRIPTION OF THE PREFERRED EMBODIMENTS

The energy dependence of the X-ray linear attenuation coefficient $\mu$ is separated into two parts:

$$\mu = \mu_p + \mu_c \tag{1}$$

where $\mu_c$ is the Klein-Nishina function for Compton scattering multiplied by electron density, and $\mu_p$ represents photoelectric absorption (including coherent scattering and binding energy corrections). The photoelectric and Compton contributions are expressed in the form:

$$\mu = aZ^m \rho + b\rho \tag{2}$$

where Z is the atomic number, m is a constant in the range of 3.0 to 4.0, $\rho$ is the electron density, and a and b are energy-dependent coefficients. We have found that m equal to 3.0 gives satisfactory results in the analysis of core samples from a borehole. It should be noted that the specific choice of m depends upon the atomic numbers included in the regression of the photoelectric coefficients. Equation (2) depends on the fact that the energy dependence of the photoelectric cross section is the same for all elements.

For a single element, Z in equation (2) in the actual atomic number. For a mixture containing several elements, the effective atomic number $Z^*$ is defined as:

$$Z^* = \sqrt[m]{\sum_i f_i Z_i^m} \tag{3}$$

where $f_i$ is the fraction of electrons on the $i^{th}$ element of atomic number $Z_i$, relative to the total number of electrons in the mixture, that is, $$f_i = \frac{n_i Z_i}{\sum_i n_i Z_i} \tag{4}$$

where $n_i$ is the number of moles of element i.

The method of the present invention consists of utilizing a CAT to image a specimen at a high and low X-ray energy level. The energies are chosen to maximize the difference in photoelectric and Compton contributions while still allowing sufficient photon flux to obtain good image quality at the lower X-ray energy. Letting 1 and 2 denote the high and low energy images and dividing equation (2) by $\rho$, the following relationships are obtained $$\mu_1/\rho = a_1 Z^3 + b_1 \tag{5a}$$

$$\mu_2/\rho = a_2 Z^3 + b_2 \tag{5b}$$

Energy coefficients ($a_1$, $b_1$) and ($a_2$, $b_2$) are determined by linear regression of $\mu/\rho$ on $Z^3$ for the high and low energy images, respectively, of calibration materials with a range of known atomic numbers and densities. Once ($a_1$, $b_1$) and ($a_2$, $b_2$) are determined, a material of unknown electron density, $\rho_x$, and effective atomic number, $Z_x^*$, can be analyzed in terms of the measured attenuation coefficients $\mu_{1x}$, $\mu_{2x}$:

$$\rho_x = \frac{a_1 \mu_{2x} - a_2 \mu_{1x}}{(a_1 b_2 - a_2 b_1)} \tag{6a}$$

$$Z_x^* = \sqrt[3]{\frac{1}{a_1}\left(\frac{\mu_{1x}}{\rho} - b_1\right)} = \sqrt[3]{\frac{-b_1 \mu_{2x} + b_2 \mu_{1x}}{a_1 \mu_{2x} - a_2 \mu_{1x}}} \tag{6b}$$

Equations (5a) and (5b) are applied to each corresponding pixel of the high and low energy images; these computations can be performed on a minicomputer or other suitable means.

Figure 1:
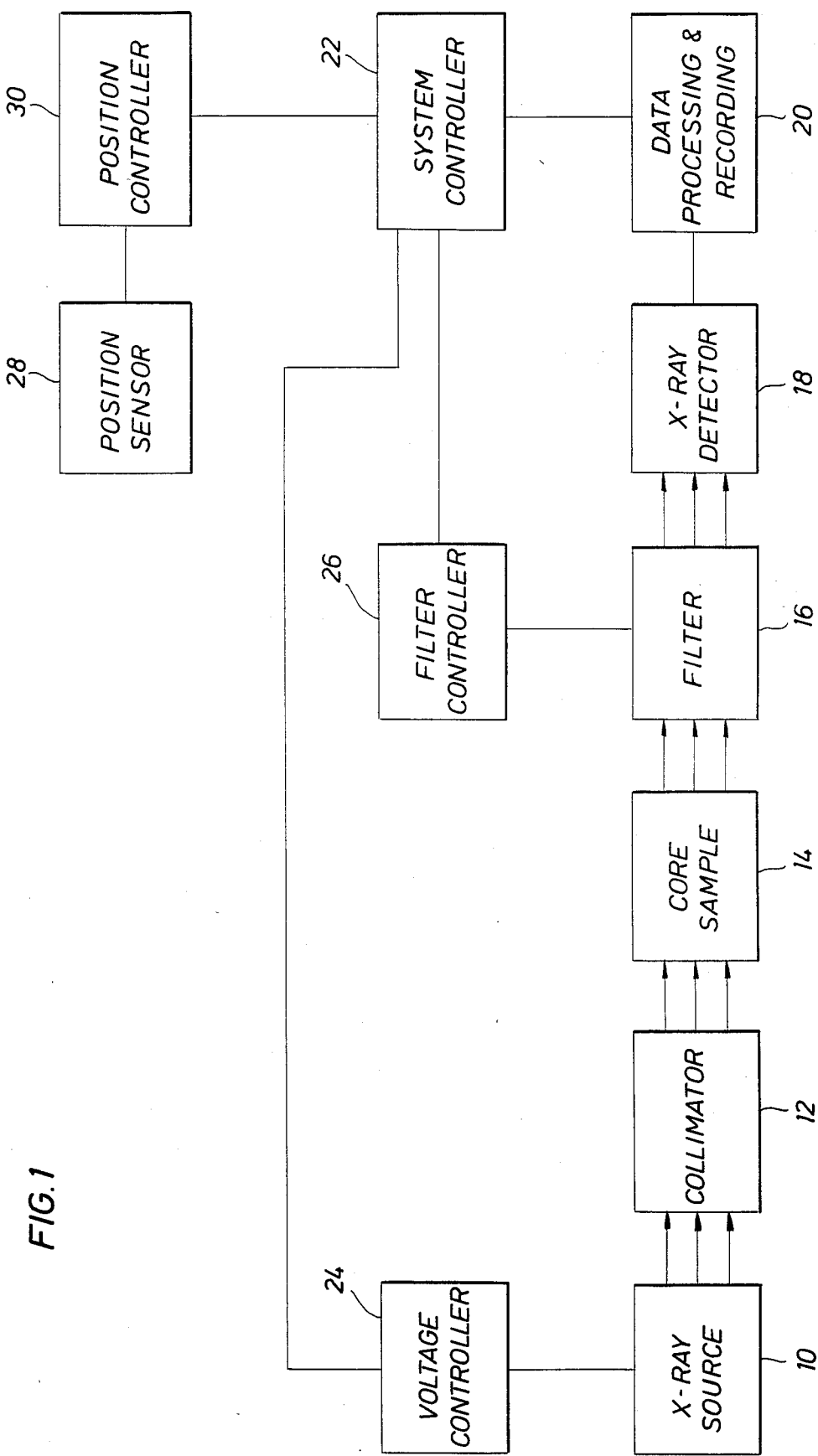
FIG. 1 is a block diagram of the computerized axial tomographic analyzer utilized in the method of the present invention.
Figure 2:
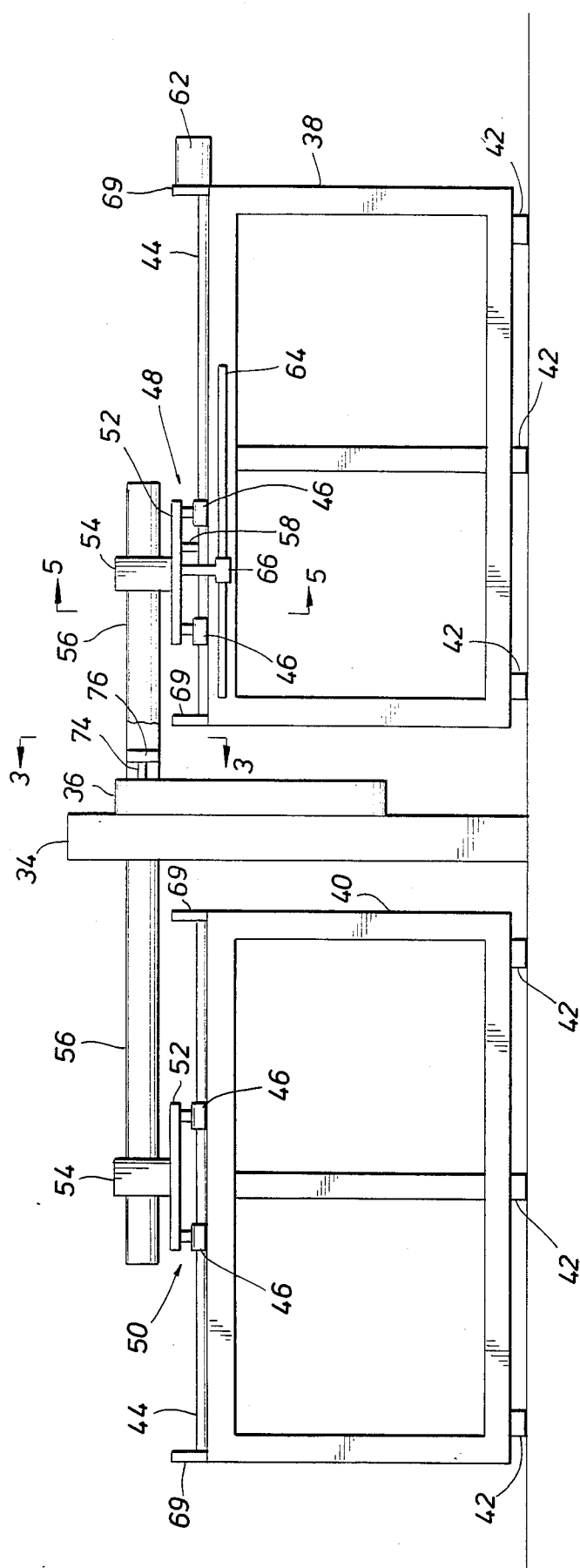
FIG. 2 is a side view of the sample holding apparatus employed with the computerized axial tomographic analyzer.
Figure 3:
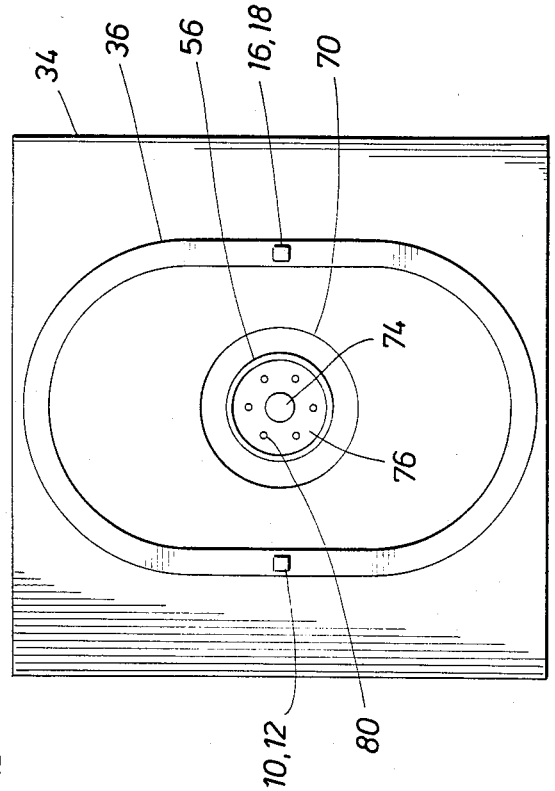
FIG. 3 is a cross sectional view taken along lines 3—3 of FIG. 2.
Figure 4:
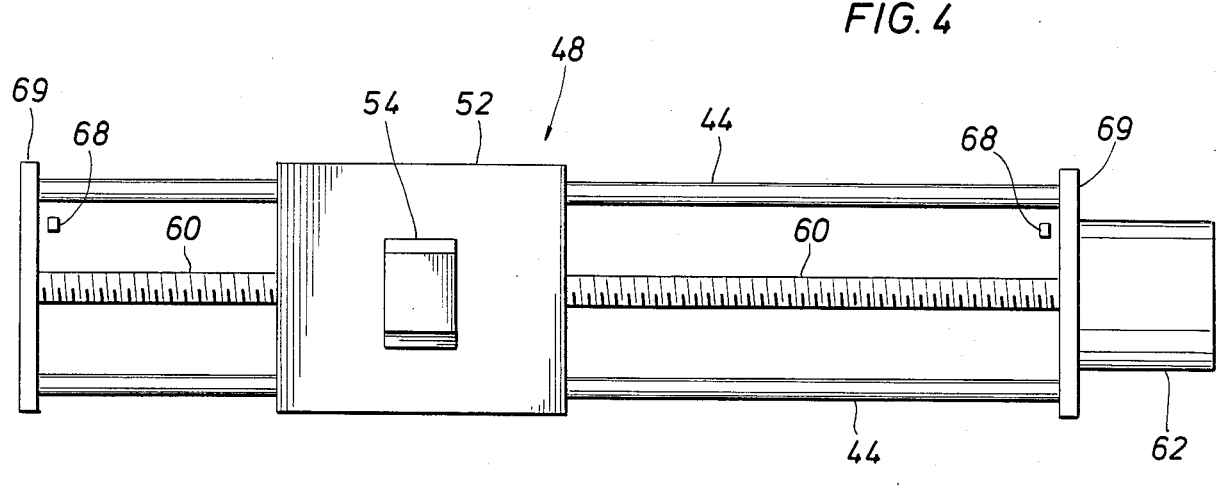
FIG. 4 is a top view of the motorized side of the sample holding apparatus.
Figure 5:
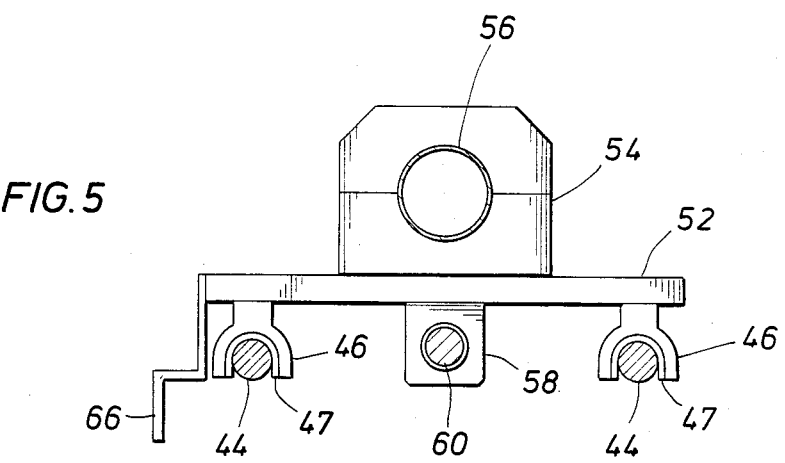
FIG. 5 is a cross sectional view taken along lines 5—5 of FIG. 2.
Figure 6:
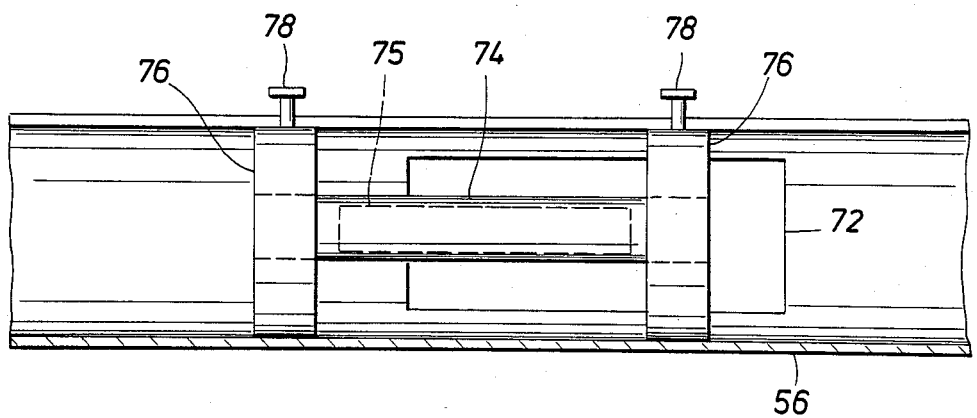
FIG. 6 is a side view of the tube and cylinder portion of the sample holding apparatus.

Referring to FIG. 1, the method of the present invention employs a CAT having an X-ray source 10 to provide X-rays which are indicated by a plurality of arrows; these X-rays are collimated by collimator 12 prior to passing through core sample 14. After the X-rays have passed through core sample 14, they are filtered by filter 16 which can be, for example, air, tungsten or copper. Alternatively, filter 16 can be applied to the X-rays prior to their entering core sample 14 rather than after their passage through core sample 14. The filtered X-rays are then detected by X-ray detectors 18 which generate signals indicative thereof; these signals are provided to suitable data processing and recording equipment 20. The entire operation, from the generation of the X-rays to the processing of the data is under the control of system controller 22. Suitable signals are provided by system controller 22 to voltage controller 24 which controls the voltage applied to X-ray source 10, thereby controlling the energy range of the X-rays. Alternatively, filter 16 can be used to vary the energy range as is known in the art. System controller 22 also provides suitable control signals to filter controller 26 to apply the appropriate filter to the X-rays which have passed through core sample 14 before they are detected by X-ray detector 18. The point along core sample 14 that is being analyzed is detected by sample position sensor 28 which provides signals indicative thereof to sample position controller 30. System controller 22 provides signals which are indicative of the desired point along core sample 14 or the amount of advancement from the last point analyzed, to sample position controller 30, which moves core sample 14 to the proper location.

Referring now to FIGS. 2-6, a suitable CAT and sample positioning system for use in the present invention is shown in detail. A typical CAT, for example, the Deltascan-100 manufactured by Technicare Corporation of Cleveland, Ohio is indicated by numeral 34. CAT 34 has a gantry 36 which contains X-ray source 10, collimator 12, filter 16 and X-ray detectors 18. Support structures or tables 38 and 40 are located on opposite sides of CAT 34 and have legs 42 which are suitably attached to, for example, the floor, to ensure that tables 38 and 40 maintain proper positioning and alignment with CAT 34. Tables 38 and 40 each have a set of guide means or rails 44, such as one inch diameter solid 60 case shafts mounted on shaft supports, Model No. SR-16, both being manufactured by Thomson Industries, Inc. of Manhasset, N.Y., on which the legs 46 of trolleys 48 and 50 ride. Preferably, legs 46 have a contact portion 47 that includes ball bearings in a nylon enclosure, such as the Ball Bushing Pillow Block, Model No. PBO-16-OPN, which are also manufactured by Thomson. Trolleys 48 and 50 have a flat member 52 which is attached to legs 46 such that member 52 is parallel to rails 44. A member 54 which can consist of two pieces fastened together by suitable means, such as screws, is mounted on member 52 and has an aperture suitable for holding tube 56. Member 52 of trolley 48 has a member 58 attached to the bottom portion of member 52 that is provided with suitable screw threads for mating with gear or screw 60. Screw 60 is driven by motor 62 for moving trolley 48 horizontally. Screw 60 can be, for example, a preloaded ball bearing screw, Model No. R-0705-72-F-W, manufactured by Warner Electric Brake & Clutch Company of Beloit, Wis., and motor 62 can be, for example, a DC motor, Model No. 1165-01DCMO/E1000MB/X2, marketed by Aerotech, Inc. of Pittsburgh, Pa. Motor 62 turns a predetermined number of degrees of revolution in response to a signal from sample position controller 30 of FIG. 1, which can be, for example, a Unidex Drive, Model No. Sa/SL/C/W/6020/DC-0/F/BR/R*, which is also marketed by Aerotech. Table 38 and trolley 48 also contain an optical encoding position sensing system, for example, the Acu-Rite-II manufactured by Bausch and Lomb Company of Rochester, N.Y., which comprises a fixed ruler or scale 64 attached to table 38 and an eye or sensor 66 attached to member 52 of trolley 48 for determining the position along ruler 64 at which trolley 48 is located. The digital output from optical sensor 66 is provided to sample position controller 30 of FIG. 1 so that sample position controller 30 can compare this with the desired position indicated by the digital signal from system controller 22 and provide appropriate control signals to motor 62 for rotation of screw 60 to accurately position trolley 48. Table 38 can also be provided with limit switches 68 which provide appropriate control signals to sample position controller 30 which limits the length of travel of trolley 48 from hitting stops 69 on table 38.

Tube 56 is centered in the X-ray field 70 of CAT 34. The attachment of tube 56 to members 54 of trolley 48 and 50 by a screw or other suitable fastening means causes trolley 50 to move when trolley 48 is moved by means of screw 60 and motor 62. Tube 56 which preferably is made of material that is optically transparent and mechanically strong and has a low X-ray absorption, for example, plexiglas, has a removable window 72 to facilitate the positioning of sample holder 74 in tube 56. A core sample 75 is positioned in sample holder 74 as indicated by dotted lines. The ends of sample holder 74 are positioned in central apertures of discs 76, which can be made of a low friction material, for example, nylon, and are sized such that they make a close sliding fit to ensure centering of the sample inside tube 56. Discs 76 are locked in position in tube 56 by screws 78 which can be made of, for example, nylon. In addition, discs 76 can be provided with a plurality of apertures 80 sized to accommodate fluid lines and electrical power lines from various equipment associated with sample holder 74.

Sample holder 74 can be a pressure-preserving, core-sample container used in normal coring operations; however, if standard X-ray energy associated with CAT scan analytic equipment, such as the Deltascan-100 mentioned hereinabove, is used the pressure vessel must be made of material that will allow the X-rays to pass through the container walls, for example aluminum, beryllium or alumina. Aluminum is preferred because it absorbs a portion of the low energy spectra, thus making the beam more monochromatic. Nevertheless, steel pressure containers can be employed if higher energy X-ray tubes or radioactive sources are used. Alternatively, sample holder 74 can be replaced by any unpressurized or unsealed container which is suitable for holding a core sample or other material in a fixed position. In the case of a frozen core sample the container can be positioned inside an insulating cylinder which can be made of, for example, styrofoam or other insulating materials with low X-ray absorption. This insulating cylinder can be filled with dry ice or the like to keep the core sample frozen. If it is desired to heat a core sample, a heating element which has a low X-ray absorption, such as the heating foil manufactured by Minco Products, Inc. of Minneapolis, Minn., can be wrapped around the container to heat the sample and a similar insulating cylinder can be used.

Figure 7:
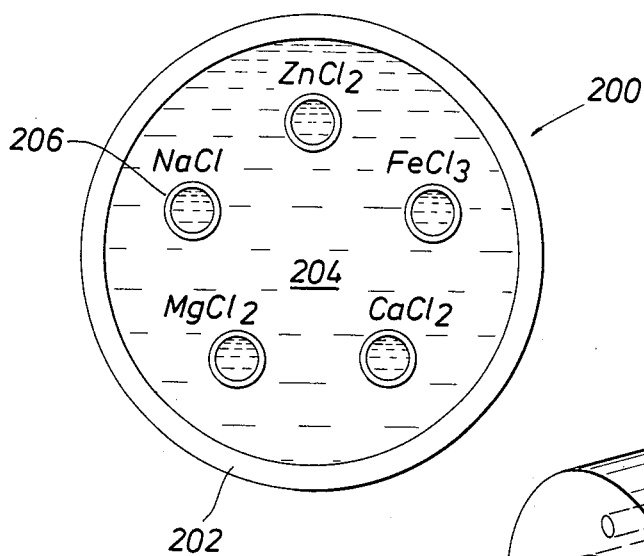
FIG. 7 shows an exemplary phantom for use with the method of the present invention.

FIG. 7 shows an exemplary phantom 200 used in the method of the present invention to determine energy-dependent coefficients a and b. Phantom 200 consists of a housing 202 made of, for example, plexiglas, which is filled with a liquid 204, for example, water. A number, in this case five of, smaller containers or vials 206 are positioned in liquid 204. Each vial 206 is filled with suitable calibration materials for the sample to be analyzed which have known densities and effective atomic numbers. The range of the effective atomic numbers should be chosen to span those of the sample being tested. For example, as shown in FIG. 7, vials 206 can be filled with $NaCl$, $MgCl_2$, $CaCl_2$, $FeCl_3$ and $ZnCl_2$ brines of known densities and effective atomic numbers.

Figure 8:
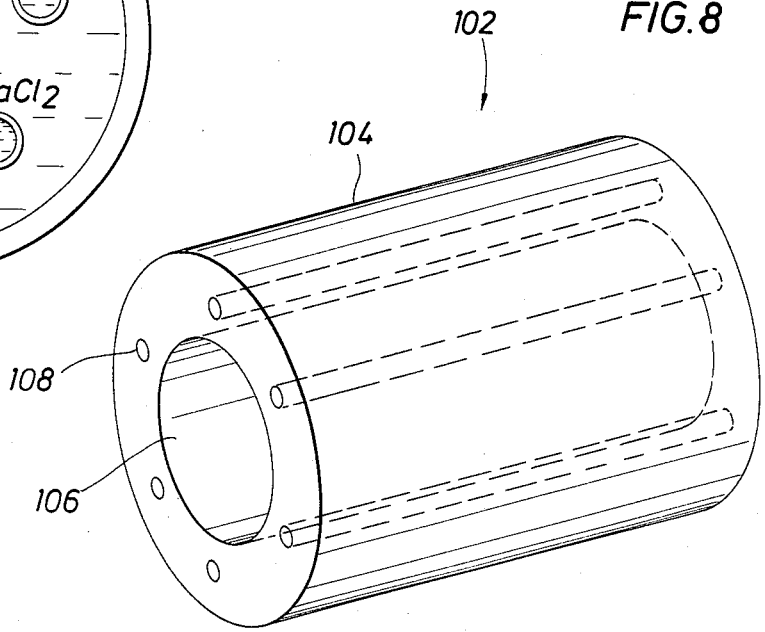
FIG. 8 shows a preferred embodiment of a phantom for use with the method of the present invention.

FIG. 8 illustrates a preferred embodiment of a phantom for use with the method of the present invention. Calibration phantom 102 consists of a cylinder 104 which has an aperture 106 that is suitably sized for holding a sample or sample container. Cylinder 104 which can be made of, for example, plexiglas or other suitable material having low X-ray absorption, contains a plurality of vials or rods 108. Vials or rods 108 should contain or be made of material that is expected to be found in the sample under test. The calibration materials in vials or rods 108 have known densities and effective atomic numbers and should be at least as long as the sample under test. For example, if a core sample is to be analyzed rods 108 can be made of aluminum, carbon, fused quartz, crystalline quartz, calcium carbonate, magnesium carbonate and iron carbonate. Alternatively, vials 108 could contain suitable liquid materials. Referring to FIGS. 2-6 and 8, cylinder 104 can take a number of different embodiments, for example, cylinder 104 can be positioned around tube 56 or it can be an integral part of tube 56. Still further, it can be an integral part of sample holder 74 or positioned in some other known relation in X-ray field 70. It should be noted that calibration phantom 102 is scanned at the same time that the sample is scanned.

Figure 9:
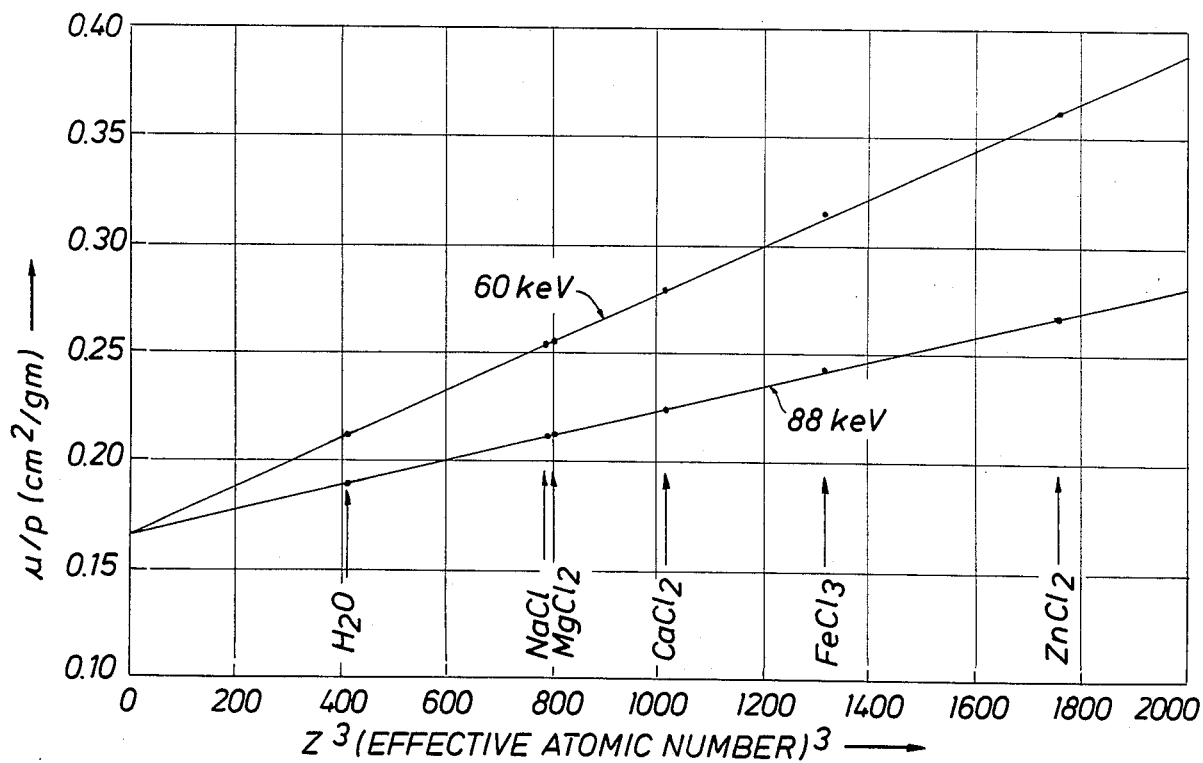
FIG. 9 shows a plot of the linear regression of $\mu/\rho$ on the effective atomic number at 60 and 88 keV mean X-ray tube energies.

FIG. 9 shows a plot of the linear regression of $\mu/\rho$ on the effective atomic number at 60 and 88 keV mean X-ray energies for phantom 200 of FIG. 7. The unknown sample is then scanned by the CAT at both energies and the measured attenuation coefficients from this scanning of the unknown sample along with the energy coefficients ($a_1$, $b_1$) and ($a_2$, $b_2$) which were previously determined are used in equations (6a) and (6b) to determine the density and atomic number for the unknown sample.

The method described hereinabove assumes that the unknown sample does not alter the spectrum of the X-ray beam. For large samples with strong attenuation, an external filter of either aluminum, copper, tungsten or other materials may be required to make the X-ray beam more monochromatic. For optimum results, the calibration should be performed under similar conditions to the measurement of the unknown material. One way to achieve this is by employing calibration phantom 102 of FIG. 8 so that several rods or vials of known density and atomic number are imaged along with the sample to provide the atomic number calibration data for equations (6a) and (6b).

It should be noted that throughout the discussion of the preferred embodiment reference has been made to a core sample from a borehole; however, this reference is merely exemplary and is not intended as a limitation of the method of the present invention. In addition, it is to be understood that variations and modifications of the present invention can be made without departing from the scope of the invention. It is also to be understood that the scope of the invention is not to be interpreted as limited to the specific embodiments disclosed herein, but only in accordance with the appended claims when read in light of the foregoing disclosure.

What is claimed is:

1. A method of obtaining an atomic number image of an unknown material, said method comprising the steps of: scanning a plurality of calibration materials with a computerized axial tomographic scanner (CAT) at a first energy, said plurality of calibration materials having a plurality of different known atomic numbers, $Z_i$, and densities, $\rho_i$; scanning said plurality of calibration materials with a CAT at a second energy; determining from attenuation coefficients from reconstructed images of said plurality of calibration materials at said first and second energies two energy-dependent coefficients, a and b, at said first and second energies according to the following equation $$\mu_i = aZ^m_i \rho_i + b\rho_i$$

where $\mu_i$: attenuation coefficient for the $i^{th}$ calibration material a: energy-dependent coefficient $Z_i$: atomic number for the $i^{th}$ calibration material m: constant in the range of 3.0–4.0

$\rho_i$: electron density for the $i^{th}$ calibration material b: energy-dependent coefficient; and scanning said unknown material with a CAT at said first energy; scanning said unknown material with a CAT at said second energy; and using said two determined energy coefficients and attenuation coefficients from reconstructed images for said unknown material at said first and second energies to determine an atomic number image of said unknown material.

2. A method as recited in claim 1, wherein said steps of scanning said plurality of calibration materials and said unknown material with a CAT at said first energy comprise scanning said plurality of calibration materials and said unknown material with a CAT at a mean energy in the range from about 80 kiloelectronvolts to about 1 megaelectronvolt and said steps of scanning said plurality of calibration materials and said unknown material at said second energy comprise scanning said plurality of calibration materials and said unknown material with a CAT at a mean energy that is less than 80 kiloelectronvolts.

3. A method as recited in claim 2, wherein said step of determining said two energy-dependent coefficients at said first and second energies comprises determining the energy-dependent coefficients at said first and second energies according to said equation where m is equal to 3.0.

4. A method as recited in claim 6, where said step of using said two determined energy coefficients and attenuation coefficients for said unknown material at said first and second energies to determine an atomic number image of said unknown material comprises determining said atomic number image according to the following equation for each of the plurality of points in the atomic number image cross section $$Z_x^* = \sqrt[m]{\frac{-b_1\mu_{2x} + b_2\mu_{1x}}{a_1\mu_{2x} - a_2\mu_{1x}}}$$

where $Z_x^*$: effective atomic number for said unknown material m: constant equal to 3.0

$a_1$: determined energy coefficient at said first energy $a_2$: determined energy coefficient at said second energy $b_1$: determined energy coefficient at said first energy $b_2$: determined energy coefficient at said second energy $\mu_{1x}$: attenuation coefficient for said unknown material at said first energy $\mu_{2x}$: attenuation coefficient for said unknown material at said second energy.

5. A method as recited in claim 4, wherein said unknown material comprises a core sample from a borehole.

6. A method as recited in claim 1, wherein said step of determining said two energy-dependent coefficients at said first and second energies comprises determining the energy-dependent coefficients at said first and second energies according to said equation where m is equal to 3.0.

7. A method as recited in claim 6, wherein said step of using said two determined energy coefficients and attenuation coefficients for said unknown material at said first and second energies to determine an atomic number image of said unknown material comprises determining said atomic number image according to the following equation for each of the plurality of points in the atomic number image cross section $$Z_x^* = \sqrt[m]{\frac{-b_1\mu_{2x} + b_2\mu_{1x}}{a_1\mu_{2x} - a_2\mu_{1x}}}$$

where $X_x^*$: effective atomic number for said unknown material m: constant equal to 3.0

$a_1$: determined energy coefficient at said first energy $a_2$: determined energy coefficient at said second energy $b_1$: determined energy coefficient at said first energy $b_2$: determined energy coefficient at said second energy $\mu_{1x}$: attenuation coefficient for said unknown material at said first energy $\mu_{2x}$: attenuation coefficient for said unknown material at said second energy.

8. A method as recited in claim 7, wherein said unknown material comprises a core sample from a borehole.

9. A method as recited in claim 1, wherein said step of using said two determined energy coefficients and attenuation coefficients for said unknown material at said first and second energies to determine an atomic number image of said unknown material comprises determining said atomic number image according to the following equation for each of the plurality of points in the atomic number image cross section $$Z_x^* = \sqrt[m]{\frac{-b_1\mu_{2x} + b_2\mu_{1x}}{a_1\mu_{2x} - a_2\mu_{1x}}}$$

where $Z_x^*$: effective atomic number for said unknown material m: constant in the range of 3.0-4.0

$a_1$: determined energy coefficient at said first energy $a_2$: determined energy coefficient at said second energy $b_1$: determined energy coefficient at said first energy $b_2$: determined energy coefficient at said second energy $\mu_{1x}$: attenuation coefficient for said unknown material at said first energy $\mu_{2x}$: attenuation coefficient for said unknown material at said second energy.

10. A method as recited in claim 1, wherein said unknown material comprises a core sample from a borehole.

11. A method as recited in claim 1, wherein said determining said two energy-dependent coefficients employs linear regression techniques.

12. A method of obtaining a density image of an unknown material that is corrected for the effects of atomic composition of said unknown material, said method comprising the steps of: scanning a plurality of calibration materials with a computerized axial tomographic scanner (CAT) at a first energy, said plurality of calibration materials having a plurality of different known atomic numbers, $Z_i$, and densities, $\rho_i$; scanning said plurality of calibration materials with a CAT at a second energy; determining from attenuation coefficients from reconstructed images of said plurality of calibration materials at said first and second energies two energy-dependent coefficients, a and b, at said first and second energies according to the following equation $$\mu_i = aZ^m_i\rho_i + b\rho_i$$

where $\mu_i$: attenuation coefficient for the $i^{th}$ calibration material a: energy-dependent coefficient $Z_i$: atomic number for the $i^{th}$ calibration material m: constant in the range of 3.0-4.0

$\rho_i$: electron density of the $i^{th}$ calibration material b: energy-dependent coefficient; and scanning said unknown material with a CAT at said first energy; scanning said unknown material with a CAT at said second energy; and using said two determined energy coefficients and attenuation coefficients from reconstructed images for said unknown material at said first and second energies to determine a density image of said unknown material.

13. A method as recited in claim 12, wherein said steps of scanning said plurality of calibration materials and said unknown material with a CAT at said first energy comprise scanning said plurality of calibration materials and said unknown material with a CAT at a mean energy in the range from about 80 kiloelectronvolts to about 1 megaelectronvolt and said steps of scanning said plurality of calibration materials and said unknown material at said second energy comprise scanning said plurality of calibration materials and said unknown material with a CAT at a mean energy that is less than 80 kiloelectronvolts.

14. A method as recited in claim 13, wherein said step of determining said two energy-dependent coefficients at said first and second energies comprises determining the energy-dependent coefficients at said first and second energies according to said equation where m is equal to 3.0.

15. A method as recited in claim 14, wherein said step of using said two determined energy coefficients and attenuation coefficients for said unknown material at said first and second energies to determine a corrected density image of said unknown material comprises determining said density image according to the following equation for each of the plurality of points in the density image cross section $$\rho_x = \frac{a_1\mu_{2x} - a_2\mu_{1x}}{a_1b_2 - a_2b_1}$$

where $\rho_x$: corrected density for said unknown material $a_1$: determined energy coefficient at said first energy $a_2$: determined energy coefficient at said second energy $b_1$: determined energy coefficient at said first energy $b_2$: determined energy coefficient at said second energy $\mu_{1x}$: attenuation coefficient for said unknown material at said first energy $\mu_{2x}$: attenuation coefficient for said unknown material at said second energy.

16. A method as recited in claim 15, wherein said unknown material comprises a core sample from a borehole.

17. A method as recited in claim 12, wherein said step of determining said two energy-dependent coefficients at said first and second energies comprises determining the energy-dependent coefficients at said first and second energies according to a said equation where m is equal to 3.0.

18. A method as recited in claim 17, wherein said step of using said two determined energy coefficients and attenuation coefficients for said unknown material at said first and second energies to determine a corrected density image of said unknown material comprises determining said density image according to the following equation for each of the plurality of points in the density image cross section $$\rho_x = \frac{a_1\mu_{2x} - a_2\mu_{1x}}{a_1b_2 - a_2b_1}$$

where
- $\rho_x$: corrected density for said unknown material
- $a_1$: determined energy coefficient at said first energy
- $a_2$: determined energy coefficient at said second energy
- $b_1$: determined energy coefficient at said first energy
- $b_2$: determined energy coefficient at said second energy
- $\mu_{1x}$: attenuation coefficient for said unknown material at said first energy
- $\mu_{2x}$: attenuation coefficient for said unknown material at said second energy.

19. A method as recited in claim 18, wherein said unknown material comprises a core sample from a borehole.

20. A method as recited in claim 12, wherein said step of using said two determined energy coefficients and attenuation coefficients for said unknown material at said first and second energies to determine a corrected density image of said unknown material comprises determining said density image according to the following equation for each of the plurality of points in the density image cross section $$\rho_x = \frac{a_1 \mu_{2x} - a_2 \mu_{1x}}{a_1 b_2 - a_2 b_1}$$

where
- $\rho_x$: corrected density for said unknown material
- $a_1$: determined energy coefficient at said first energy
- $a_2$: determined energy coefficient at said second energy
- $b_1$: determined energy coefficient at said first energy
- $b_2$: determined energy coefficient at said second energy
- $\mu_{1x}$: attenuation coefficient for said unknown material at said first energy
- $\mu_{2x}$: attenuation coefficient for said unknown material at said second energy.

21. A method as recited in claim 12, wherein said unknown material comprises a core sample from a borehole.

22. A method as recited in claim 12, wherein said determining said two energy-dependent coefficients employs linear regression techniques.

23. A method of obtaining an atomic number image of an unknown material, comprising:
scanning a plurality of calibration materials having known different atomic numbers, $Z_i$, and densities, $\rho_i$, and said unknown material at a first energy with a computerized axial tomograph (CAT) scanner,
scanning said plurality of calibration materials and said unknown material at a second energy with said CAT scanner,
calculating two energy-dependent coefficients from attenuation coefficients of said calibration materials obtained from reconstructed images of said calibration materials at said first and second energies, and
calculating an effective atomic number image for said unknown material from attenuation coefficients for said unknown material obtained from reconstructed images of said unknown material and said energy-dependent coefficients at said first and second energies.

24. A method of obtaining a density image of an unknown material, comprising;
scanning a plurality of calibration materials having known different atomic numbers, $Z_i$, and densities, $\rho_i$, and said unknown material at a first energy with a computerized axial tomograph (CAT) scanner,
scanning said plurality of calibration materials and said unknown material at a second energy with said CAT scanner,
calculating two energy-dependent coefficients from attenuation coefficients of said calibration materials obtained from reconstructed images of said calibration materials at said first and second energies, and
calculating a density image for said unknown material from attenuation coefficients for said unknown material obtained from reconstructed images of said unknown material and said energy-dependent coefficients at said first and second energies.

* * * * *